(12) United States Patent
Otley

(10) Patent No.: US 9,332,978 B2
(45) Date of Patent: *May 10, 2016

(54) VEIN CLOSURE AND INJECTION KITS AND METHODS

(71) Applicant: Mayo Foundation for Medical Education and Research, Rochester, MN (US)

(72) Inventor: Clark C. Otley, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/104,121

(22) Filed: Dec. 12, 2013

(65) Prior Publication Data

US 2014/0100460 A1    Apr. 10, 2014

Related U.S. Application Data

(63) Continuation of application No. 12/093,114, filed as application No. PCT/US2006/043607 on Nov. 9, 2006, now Pat. No. 8,632,520.

(60) Provisional application No. 60/735,983, filed on Nov. 10, 2005.

(51) Int. Cl.
*A61B 17/12* (2006.01)
*A61M 25/01* (2006.01)
(Continued)

(52) U.S. Cl.
CPC ............. *A61B 17/0057* (2013.01); *A61B 17/04* (2013.01); *A61B 17/08* (2013.01);
(Continued)

(58) Field of Classification Search
CPC ............. A61B 17/00008; A61B 17/12; A61B 17/1285; A61B 17/12009; A61B 17/04; A61B 17/08; A61B 17/0057; A61B 18/00
USPC ............... 604/507, 508, 510, 164.09, 164.11, 604/164.01
See application file for complete search history.

(56) References Cited

U.S. PATENT DOCUMENTS 4,101,063 A      7/1978   Kapitanov et al.
5,261,889 A  *  11/1993   Laine ..................... A61B 1/015
                                                           600/104
(Continued)

FOREIGN PATENT DOCUMENTS

WO        2005/053547 A2     6/2005

OTHER PUBLICATIONS

Rotter et al. "Human saphenous vein in vitro model for sudying the action of sclerosing solutions." J. Dermatology Surg. Oncol. 1993; 19(1): 59-62.*

(Continued)

*Primary Examiner* — Bhisma Mehta
*Assistant Examiner* — Jenna Zhang
(74) *Attorney, Agent, or Firm* — Mueting, Raasch & Gebhardt, P.A.

(57) ABSTRACT

Kits, apparatus, devices and methods for treating varicose veins caused by an incompetent venous junction (e.g., the saphenofemoral and/or saphenopopliteal junctions) are disclosed. The kits may include a sheath, a vein closure device, and an injection device. Alternatively, a vein closure device may include an integral injection channel and injection device. Methods may include injecting a vein with a sclerosing agent through a needle that extends in a direction that is not aligned with a longitudinal axis of a sheath or shaft.

15 Claims, 4 Drawing Sheets

(51) Int. Cl.
*A61B 17/00* (2006.01)
*A61B 17/04* (2006.01)
*A61B 17/128* (2006.01)
*A61B 17/08* (2006.01)
*A61B 18/00* (2006.01)
*A61M 31/00* (2006.01)
*A61M 25/00* (2006.01)
*A61M 25/10* (2013.01)

(52) U.S. Cl.
CPC ............ *A61B 17/12* (2013.01); *A61B 17/1285* (2013.01); *A61B 18/00* (2013.01); *A61M 25/0084* (2013.01); *A61B 17/12009* (2013.01); *A61B 2017/00778* (2013.01); *A61M 2025/0092* (2013.01); *A61M 2025/1052* (2013.01)

(56) References Cited

U.S. PATENT DOCUMENTS

| | | | | |
|---|---|---|---|---|
| 5,373,840 | A * | 12/1994 | Knighton | A61B 1/018 600/106 |
| 5,611,357 | A | 3/1997 | Suval | |
| 5,643,293 | A * | 7/1997 | Kogasaka | A61B 17/0469 112/169 |
| 5,758,665 | A * | 6/1998 | Suval | A61B 17/00008 128/898 |
| 5,833,696 | A | 11/1998 | Whitfield et al. | |
| 6,106,473 | A | 8/2000 | Violante et al. | |
| 6,283,951 | B1 * | 9/2001 | Flaherty | A61M 5/46 604/164.11 |
| 6,352,544 | B1 * | 3/2002 | Spitz | A61B 17/00008 606/159 |
| 6,506,156 | B1 * | 1/2003 | Jones | A61K 49/223 600/432 |
| 6,544,185 | B2 | 4/2003 | Montegrande | |
| 6,602,251 | B2 * | 8/2003 | Burbank | A61B 8/06 128/898 |
| 6,610,016 | B1 | 8/2003 | Violante et al. | |
| 6,860,892 | B1 * | 3/2005 | Tanaka | A61B 17/00008 600/201 |
| 7,063,699 | B2 | 6/2006 | Hess et al. | |
| 7,972,265 | B1 * | 7/2011 | Chin | A61B 17/00008 600/206 |
| 8,632,520 | B2 | 1/2014 | Otley | |
| 2004/0138562 | A1 * | 7/2004 | Makower | A61M 25/0084 600/439 |
| 2006/0149218 | A1 * | 7/2006 | Slater | A61M 25/00 604/509 |
| 2007/0166345 | A1 * | 7/2007 | Pavcnik | A61B 17/12022 424/423 |

OTHER PUBLICATIONS

International Search Report / Written Opinion issued Apr. 29, 2008, International Application No. PCT/US2006/043607, filed Nov. 9, 2006; 6 pgs.

International Preliminary Report on Patentability issued Apr. 9, 2009, International Application No. PCT/US2006/043607, filed Nov. 9, 2006; 5 pgs.

Moore, "The Stripping Operation for Varicose Veins: Its Results Compared with Those of High Ligation and Retrograde Injection," *Scot. Med. J.*, 1957;2:319.

Rotter et al., "Human saphenous vein in vitro model for studying the action of sclerosing solutions," *J. Dermatology Surg. Oncol.*, 1993;19(1):59-62.

* cited by examiner

VEIN CLOSURE AND INJECTION KITS AND METHODS

RELATED APPLICATION

The present application is a continuation patent application of U.S. patent application Ser. No. 12/093,114 filed on Oct. 10, 2008, which is a U.S. National Stage Application of International Application No. PCT/US2006/043607, titled VEIN CLOSURE AND INJECTION KITS AND METHODS, filed on Nov. 9, 2006, which claims the benefit under 35 U.S.C. §119(e) of U.S. Provisional Patent Application No. 60/735,983, titled VEIN CLOSURE AND INJECTION KITS AND METHODS, filed on Nov. 10, 2005, each of which is hereby incorporated by reference in its entirety.

Varicose veins are a very common medical condition, associated with problems ranging from achy legs to recurrent dermatitis, phlebitis, and skin ulceration. Unsightly varicose veins are also a significant cosmetic problem in many patients. Significant health care expenditures are made for treatment of varicose veins. Incompetence of the saphenofemoral junction is the most common source of venous abnormalities in the lower extremities. The saphenopopliteal junction may also suffer from incompetence leading to varicose veins.

Multiple techniques have been developed to treat saphenofemoral junction incompetence. Traditionally, ligation and stripping of the saphenous vein was performed, but was a more invasive technique than most patients desired. More recently, endovenous techniques involving intraluminal catheterization and vein ablation with either laser or radiofrequency technology has been used. Although the endovenous techniques are less invasive and easier to heal from than traditional surgical stripping, these procedures can be time consuming, may be hampered by difficulty with intraluminal access, and expose patients to the risks of an intraluminal destructive procedure, which can result in deep vein thrombosis, incompetence of the saphenous vein distal to the junction has been treated with either stripping or distal continuation of endoluminal ablation. Sclerotherapy of incompetent saphenous veins can also used, but with a patent saphenofemoral junction may be associated with deep venous thrombosis or recanalization.

There are multiple disadvantages of current technology for treating varicose veins resulting from saphenofemoral junction incompetence. For ligation and stripping procedures, the disadvantages may include, e.g., high cost ($15,000 or more); risks and costs associated with general or spinal anesthesia; longer incisional scars; tissue trauma; prolonged recovery; time consuming procedure to perform; etc.

Closure through intraluminal radiofrequency (RF) ablation may suffer from the following disadvantages: high cost ($15,000 or more); difficulty with access to saphenous vein at the knee; risks associated with intraluminal ablation generally (e.g., deep venous thrombosis, vein spasms, perforation, etc.); the need for radiofrequency power source ($20,000); the need for high cost disposable catheter ($750); time consuming procedure to perform; the risk of burns associated with the use of RF energy; etc.

Endoluminal laser ablation (intraluminal) may also suffer from some of the same and other disadvantages such as, e.g., high cost ($15,000 or more); difficulty with access to saphenous vein at knee; the risks associated with intraluminal ablation (e.g., deep venous thrombosis, vein spasms, perforation, etc.), the need for laser power source; the need for high cost disposable catheter; time consuming procedure to perform; risk of burns associated with the use of laser energy; etc.

If used alone as a treatment, sclerotherapy may suffer from the following risks: deep venous thrombosis of femoral vein with nearby injection at saphenofemoral junction; failure of sclerosis or recanalization; central nervous system effects from foam injected near saphenofemoral junction; etc.

SUMMARY OF THE INVENTION

The present invention provides kits, apparatus, devices and methods for treating varicose veins caused by an incompetent venous junction (e.g., the saphenofemoral and/or saphenopopliteal junctions). The present invention addresses incompetence at the venous junction, prior to and in conjunction with treatment of distal branch veins. The systems of the present invention may also be used to address reflux at other venous sites.

Among the potential advantages of at least sonic embodiments of the present invention are, e.g., no power source required (for procedures using clips, staples, sutures, etc. to close the venous junction); reduced instrumentation costs; reduced risk of intraluminal complications (e.g., reduction in the risk of deep vein thrombosis and recanalization normally associated with sclerotherapy); relatively small access site in that may be in a discreet location (e.g., inguinal fold); performance with local anesthesia; reduced treatment time; reduced tissue trauma; securing of venous junction prior to intraluminal sclerotherapy, etc.

The vein closure devices used in connection with the present invention may rely on any suitable technique for closing a tubular organ of the appropriate size. For example, the vein closure devices may apply clips or staples to close the vein. Closure of the vein or veins may alternatively be effected by any suitable technique or combination of techniques, e.g., suture ligation, electrosurgical ablation, laser energy, radio frequency (RF) energy, etc. Examples of some potentially suitable closure techniques may be described in U.S. Pat. No. 5,611,357 (Suval); U.S. Patent Application. Publication US 2002/0099375 (Hess et al.), etc.

In one aspect, the present invention provides a vein closure and injection kit that may include an elongated sheath with a proximal end and a distal end defining a longitudinal axis extending along the elongated sheath from the proximal end to the distal end, the elongated sheath including a main channel extending along the longitudinal axis from the proximal end to the distal end of the elongated sheath, wherein the main channel has an entry port at the proximal end of the elongated sheath and an exit port at the distal end of the elongated sheath, wherein a device extending out of the main channel from the exit port is directed along the longitudinal axis. The elongated sheath may also include an injection channel extending from the proximal end of the elongated sheath towards the distal end of the elongated sheath, wherein the injection channel has an injection port in a side wall of the elongated sheath and an insertion port at the proximal end of the elongated sheath, wherein the injection port is located proximally of the exit port of the main channel and wherein a proximal portion of the injection channel extends along the longitudinal axis to a bend at which the injection channel defines an injection direction that forms an injection angle that is greater than five (5) degrees with the longitudinal axis, wherein the turn is located between the injection port and the insertion port, whereby an injection device extending out of the injection channel from the injection port is directed along the injection direction. The kit may further include a vein closure device operable through the main channel of the elongated sheath, wherein the vein closure device has an actuator that protrudes from the entry port of the main channel and a closure mechanism protruding from the exit port of the main channel during closure of a vein using the vein closure device. Still further, the kit may include an injection device operable through the injection channel of the elongated sheath, wherein the injection device includes a needle protruding from the injection port of the injection channel during injection into a vein, and wherein the injection device has a syringe body and plunger attached to a proximal end of the needle. A dissecting instrument operable through the main channel of the elongated sheath may also be included in the kit, wherein the dissecting instrument has a dissecting end that protrudes from the exit port of the main channel and a proximal end that protrudes from the entry port of the main channel during dissection of tissue using the dissecting instrument.

In various embodiments, the vein closure device may include movable jaws having open and closed configurations, wherein the injection direction lies in a plane that extends between the movable jaws when the movable jaws are in the open configuration.

Other variations may include, e.g., an elongated sheath with ultrasonically visible material; a vein closure device with ultrasonically visible material; and/or a dissecting instrument with ultrasonically visible material. The ultrasonically visible material may be in the form of a coating. The vein closure device may be a suture ligation device; a clip ligation device; an electrosurgical ablation device, etc. In another variation, the injection device is slidably mounted on the elongated sheath, whereby advancing the syringe body in the distal direction along the elongated the syringe body advances the needle out of the injection port. The elongated sheath may include an imaging channel extending along the elongated sheath, wherein the imaging channel comprises a viewing port proximate the distal end of the elongated sheath. The kit may include a vision/imaging system adapted to use the imaging channel, whereby a practitioner can visually monitor operation of the vein closure device at the distal end of the elongated sheath. The kit may also be supplied with a sclerosing agent.

In another aspect, the present invention may provide a method of treating saphenofemoral junction incompetence by advancing a distal end of an elongated sheath to a position proximate an incompetent saphenofemoral junction using a dissecting instrument located within a main channel of the elongated sheath; withdrawing the dissecting instrument; advancing a vein closure device through the main channel to the distal end of the elongated sheath; grasping the saphenous vein at a location distal to the saphenofemoral junction; advancing a needle out of an injection port of an injection channel of the elongated sheath (or integrated into the vein closure device), wherein the injection channel defines an injection direction that forms an injection angle that is greater than five (5) degrees with a longitudinal axis of the elongated sheath, whereby the needle extends out of the injection channel from the injection port along the injection direction; injecting a sclerosing agent into the saphenous vein at an injection site that is distal of the location at which the saphenous vein is grasped, wherein the injecting is performed using the needle advanced out of the injection port; withdrawing the needle into the injection channel; closing the saphenous vein at a location distal of the saphenofemoral junction and proximal of the injection site using the vein closure device; withdrawing the vein closure device and the elongated sheath; and visually monitoring the positioning of the elongated sheath, dissecting instrument, vein closure device, and needle using ultrasonic energy.

In another aspect, the present invention provides a vein closure and injection kit including an elongated sheath having a proximal end and a distal end defining a longitudinal axis extending along the elongated sheath from the proximal end to the distal end. The elongated sheath includes a main channel extending along the longitudinal axis from the proximal end to the distal end of the elongated sheath, wherein the main channel includes an entry port at the proximal end of the elongated sheath and an exit port at the distal end of the elongated sheath, wherein a device extending out of the main channel from the exit port is directed along the longitudinal axis. The elongated sheath also includes an injection channel extending from the proximal end of the elongated sheath towards the distal end of the elongated sheath, wherein a proximal portion of the injection channel extends along the longitudinal axis to a bend at which the injection channel defines an injection direction that is not aligned with the longitudinal axis, whereby an injection device extending out of the injection channel from an injection port is directed along the injection direction. The kit further includes a vein closure device operable through the main channel of the elongated sheath, wherein the vein closure device comprises an actuator that protrudes from the entry port of the main channel and a closure mechanism protruding from the exit port of the main channel during closure of a vein using the vein closure device. The kit also includes an injection device operable through the injection channel of the elongated sheath, wherein the injection device has a needle protruding from the injection port of the injection channel during injection into a vein.

In another aspect, the present invention provides a vein closure apparatus that includes a shaft having a proximal end and a distal end, wherein a longitudinal axis extends between the proximal end and the distal end of the shaft; movable jaws located at the distal end of the shaft; an actuator located at the proximal end of the shaft, the actuator operably connected to the move the movable jaws between an open configuration and a closed configuration in which a vein is secured between the jaws; an injection device having an injection needle extending out of an injection port formed in the shaft proximate the distal end of the shaft, wherein the injection needle enters the interior of the shaft proximate the proximal end of the shaft, and wherein the injection needle exits the shaft at an injection direction that is not aligned with the longitudinal axis.

In another aspect, the present invention provides a method of treating saphenofemoral junction incompetence by advancing a distal end of an elongated sheath to a position proximate an incompetent saphenofemoral junction using a dissecting instrument located within a main channel of the elongated sheath; advancing a vein closure device through the main channel to the distal end of the elongated sheath; grasping the saphenous vein at a location distal to the saphenofemoral junction; advancing a needle out of an injection port of an injection channel of the elongated sheath, wherein the injection channel defines an injection direction that is not aligned with a longitudinal axis of the elongated sheath, whereby the needle extends out of the injection channel from the injection port along the injection direction; and injecting a sclerosing agent into the saphenous vein at an injection site that is distal of the location at which the saphenous vein is grasped, wherein the injecting is performed using the needle advanced out of the injection port.

These and other potential features and advantages of the present invention may be described below in connection with the exemplary embodiments of the invention.

BRIEF DESCRIPTIONS OF THE FIGURES

DESCRIPTION OF EXEMPLARY EMBODIMENTS OF THE INVENTION

In the following description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

The present invention provides a unique approach to the treatment of venous junction incompetence, involving extraluminal endoscopic venous junction closure. The closure is combined with simultaneous retrograde sclerotherapy which accomplishes treatment of the distal incompetent saphenous vein. Because venous junction closure preferably precedes the sclerotherapy of the distal saphenous vein, the risks of deep venous thrombosis and recanalization may be reduced.

It may be preferred that the vein closure and sclerotherapy be performed with the aid of an imaging system such as, e.g., advanced duplex ultrasound technology, that allows for direct visualization of the saphenous vein and saphenofemoral junction. In that regard, it may be preferred that one or more of the devices and instruments of the present invention incorporate materials that can be detected using ultrasonic energy. Examples of some potentially suitable materials/constructions may be found in, e.g., U.S. Pat. No. 6,106,473 (Violante et al.); U.S. Pat. No. 6,506,156 (Jones et al.); and U.S. Pat. No. 6,544,185 (Montegrande).

Figure 1:
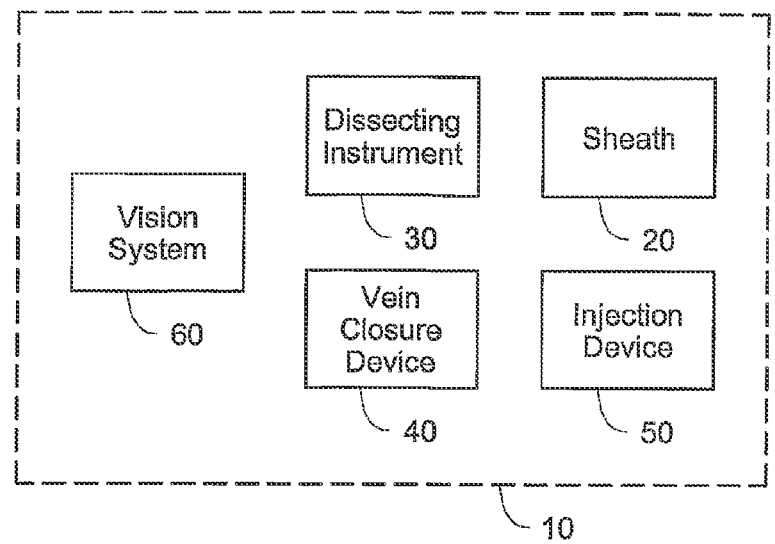
FIG. 1 is a schematic diagram of the components that may be included in a kit according to the present invention.

FIG. 1 is a block diagram illustrating some of the potential components that may be included in a kit 10 of the present invention. These components may include, e.g., a sheath 20 that can be used to introduce other devices and instruments to a desired internal body location; a dissecting instrument 30 that may, e.g., be used to obtain access to the desired internal body location; a vein closure device 40 that can be used to close a vein at one or more desired internal body locations; an injection device 50 that may be used to inject one or more sclerosing agents into one or more selected veins as a part of the procedure; and a vision system 60 that may be used to provide some imaging/visual feedback for a practitioner.

These different components may or may not be present in a kit according to the present invention. For example, the injection device 50 or vision system 60 may be supplied separately from the remainder of the kit 10. In some instances, one or more of the components, e.g. the vision system 60, may not be used at all. Furthermore, it should be understood that one or more components other than those include in the kit 10 depicted in FIG. 1 may be included in kits according to the present invention. For example, kits according to the present invention may be supplied with one or more sclerosing agents selected for use in connection with the other components of the kit.

Figure 2:
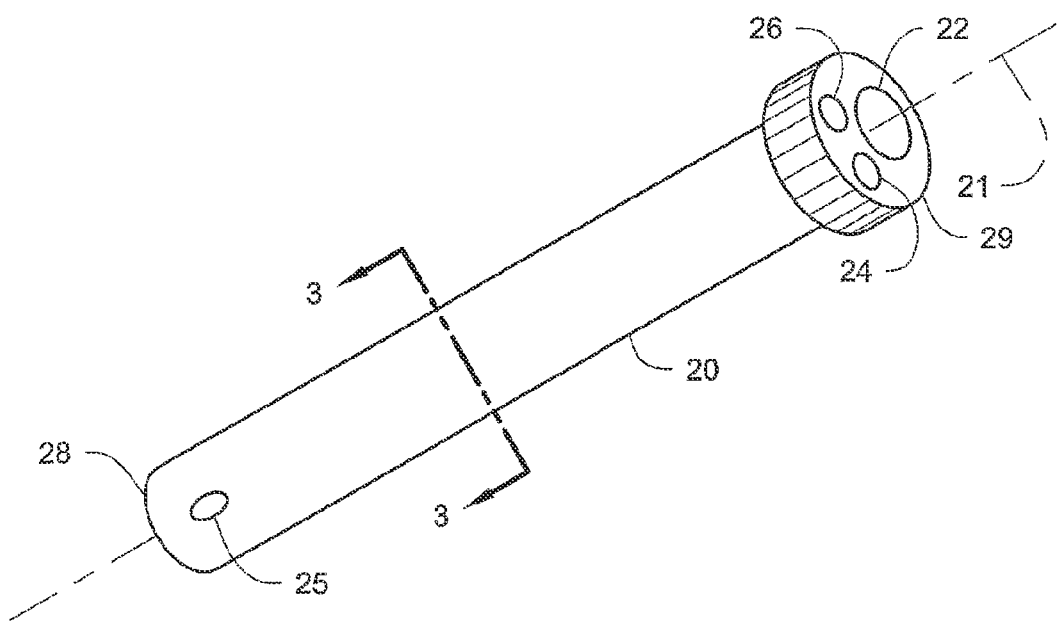
FIG. 2 is a perspective view of one outer sheath that may be used in connection with the present invention.

FIG. 2 depicts one exemplary sheath 20 that may be used in connection with the present invention. The sheath 20 may be formed as an elongated tubular body that extends along a longitudinal axis 21 and includes a main channel 22, an injection channel 24 and an imaging channel 26. The main channel 22 may preferably extend from the proximal end 29 of the sheath 20 to its distal end 28. The injection channel 24 may preferably extend along the sheath 20 to an injection port 25 at which the path of an injection device (e.g., a needle) exits the sheath 20 at an angle off of the longitudinal axis as is discussed in more detail below. The imaging channel 26 (if provided) may preferably allow access to the distal end of the sheath 20 by an imaging system (e.g., a fiberoptic system such as the Olympus plastic surgery telescope; 160 mm; Cat #A7595A or other miniature visualization system) in some embodiments, the imaging or vision system may be incorporated into the vein closure device itself.

Figure 3:
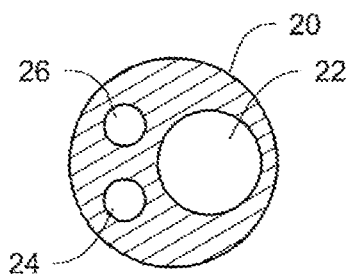
FIG. 3 is a cross-sectional view of the outer sheath of FIG. 2 taken along line 3-3 in FIG. 2.
Figure 4:
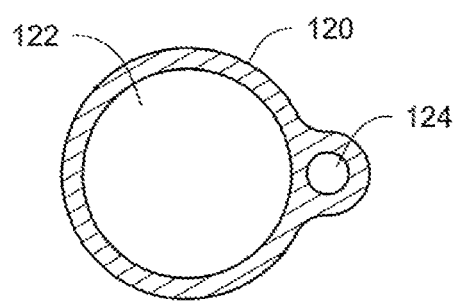
FIG. 4 is a cross-sectional view of an alternative outer sheath.

FIG. 3 is a cross-sectional view of the sheath 20 taken along line 3-3 in FIG. 2 and depicts the arrangement of the main channel 22, injection channel 24 and imaging channel 26 within the body of the sheath 20. FIG. 4 is a cross-sectional view of an alternative sheath 120 that includes a main channel 122 and an injection channel 124 in a body, the outer surface of which is not circular as is the sheath 20 of FIG. 3.

Figure 5:
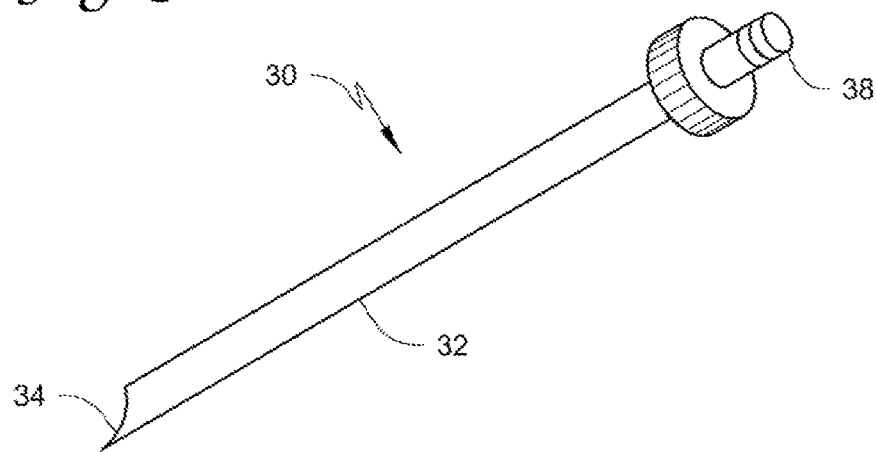
FIG. 5 is a perspective view of an exemplary dissecting instrument that may be used in connection with the present invention.

FIG. 5 depicts another exemplary component that may be included in the kits of the present invention in the form of a dissecting instrument 30. The dissecting instrument 30 may be used in connection with the sheath 20 to provide access to a desired internal body location by direct dissection of soft tissues and fascia. The dissecting instrument 30 may include one or more cutting edges at its distal end 34 and a hollow channel extending through body 32 with, e.g., a fitting 38 at the proximal end of the body 32 to allow for the introduction of a local anesthetic during insertion. The dissection instrument 30 may preferably be adapted to work through the main channel of the sheath 20.

Figure 6:
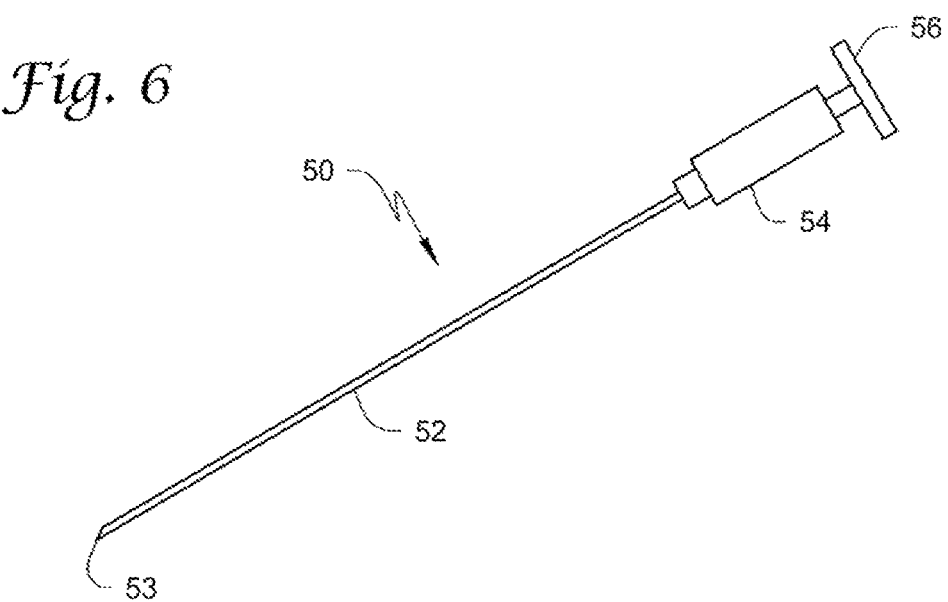
FIG. 6 depicts one exemplary injection device that may be used in connection with the present invention.

FIG. 6 depicts an exemplary injection device 50 in the form of a syringe with a needle 52 having a tip 53, a barrel 54, and a plunger 56 adapted to move materials from the barrel 54 through the needle 52.

Figure 7:
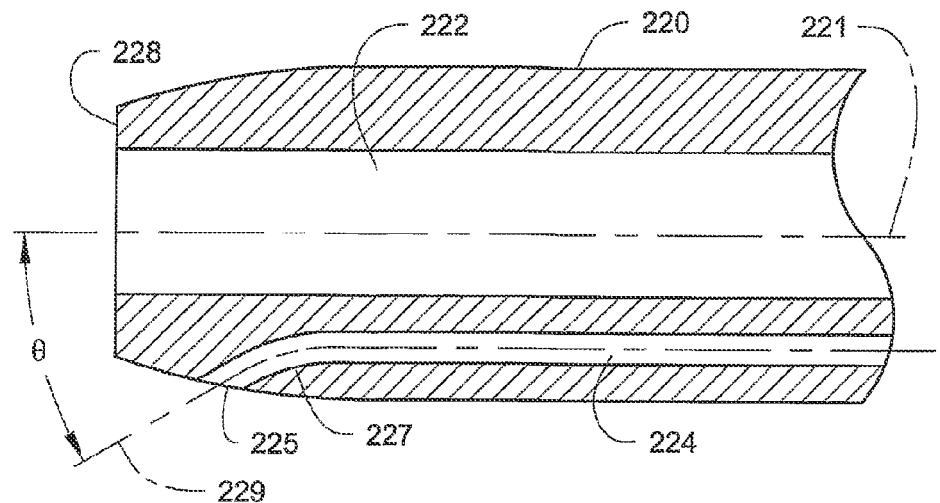
FIG. 7 is an enlarged partial cross-sectional view of the distal end of an exemplary outer sheath that may be used in connection with the present invention.

In many respects, the ability to both close a vein and provide for retrograde sclerotherapy of the distal vein relies on the spatial arrangement of a vein closure device and the injection device at the distal end of the sheath. FIG. 7 depicts a relationship between the main channel 222 of a sheath 220 that may be used in connection with the present invention. The injection port 225 (from which a needle would exit the sheath 220) is located proximally of the exit port of the main channel (located at the distal end 228 of the sheath 220). A proximal portion of the injection channel 224 extends along (preferably parallel to or otherwise substantially aligned with) the longitudinal axis 221 to a bend 227 at which the injection channel 224 defines an injection direction 229 that forms an injection angle θ (theta) with the longitudinal axis 221 that is preferably five (5) degrees or more, more preferably 10 degrees or more. The bend 227 is located between the injection port 225 and the insertion port (not shown) of the injection channel 224, whereby an injection device extending out of the injection channel 224 from the injection port 225 is directed along the injection direction (and, thus, is not parallel to or aligned with the longitudinal axis 221).

Figure 8A:
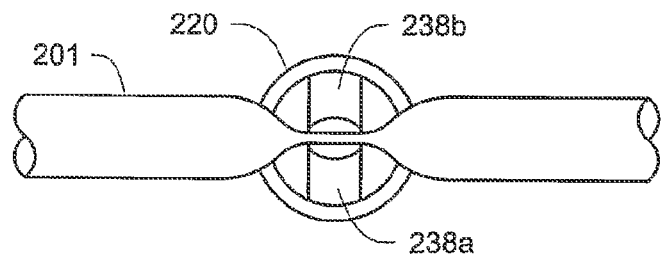
FIGS. 8A & 8B depict a portion of one exemplary procedure according to the present invention.
Figure 8B:
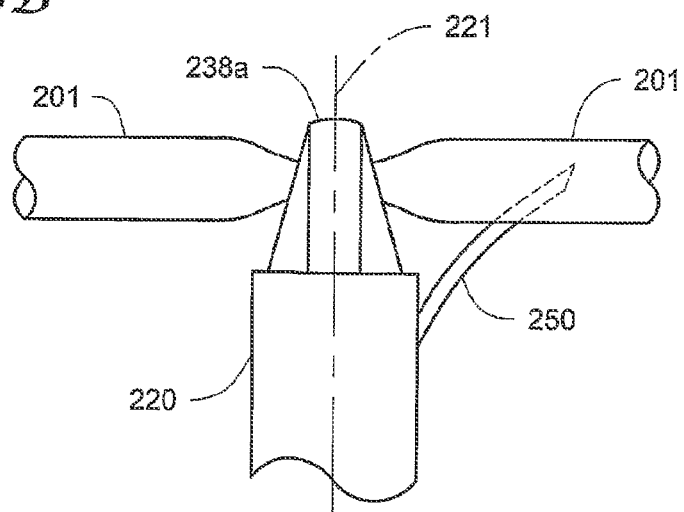

FIGS. 8A & 8B depict alternate views of one exemplary procedure in which the jaws 238a and 238b of a vein closure device extend out of a sheath 220 to close a vein 201 while a needle 250 extends into the vein on one side of the jaws to inject a sclerosing agent therein. The needle 250 extends out of the sheath 220 along an injection direction that is not aligned with the longitudinal axis 221 as discussed herein.

Figure 9:
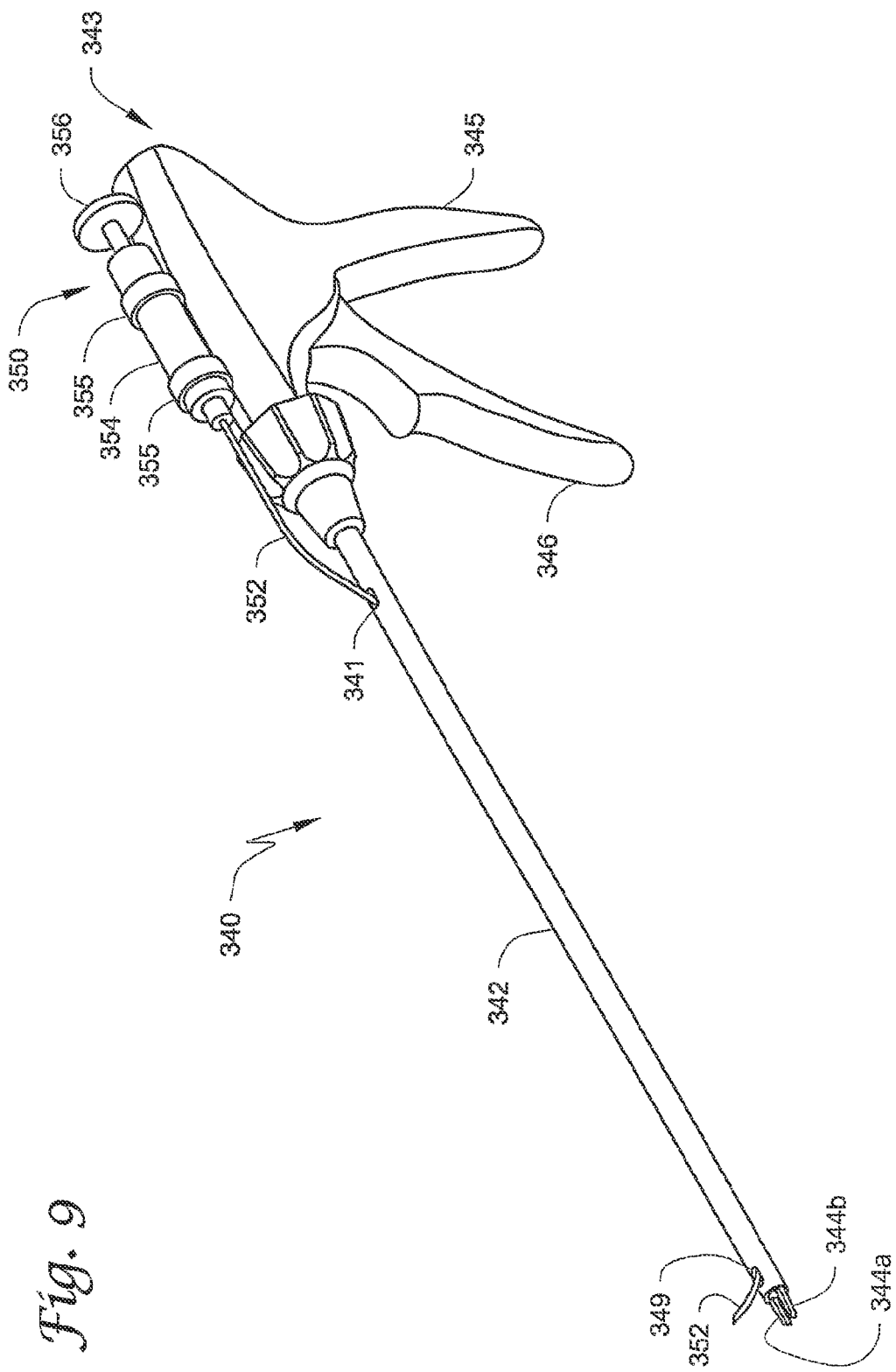
FIG. 9 is a perspective view of one exemplary vein closure device that may be used in connection with the present invention.

FIG. 9 depicts en exemplary embodiment of a vein closure device 340 that may preferably incorporate an injection channel therein. The device 340 includes a shaft 342 leading to a distal end at which jaws 344a and 344b are located. These jaws may be used to, e.g., hold a vein during a closure procedure. A handle 343 that includes a stationary portion 345 and a movable portion 346 for actuating the jaws 344a and 344b. The handle 343 may also be used to actuate a closure mechanism such as a stapler, suturing device, electrosurgical device, etc.

Also depicted in connection with the vein closure device 340 is an injection device 350 including hand 354 and plunger 356 that may be attached to the handle 343 by clips 355 or any other suitable structure. The injection device 350 preferably includes a needle 352 that extends into the interior of the shaft 342 through an opening 341 and is capable of extending back out of the shall 342 at a distal injection port 349. As a result, the shaft 342 of the closure device 340 may serve as a guide for the injection needle 352 between opening 341 and injection port 349 (in addition to providing support for the vein closure apparatus).

It may be preferred that the injection device 350 he attached to the vein closure device 340 in manner that allows for movement such that the needle is withdrawn into the shall 342 until a vein is secured between the jaws 344a & 344b. With a vein clamped between the jaws (or otherwise secured), the needle 352 of the injection device 350 may be advanced out of the shaft 342 and into the vein as is discussed herein.

Such a combination of functions is but one example of the different combinations that may be made in the components of the kits of the present invention. Providing the injection device through shaft 342 may eliminate the need for a separate injection channel in a sheath (if a sheath is used in connection with closure device 340). Another example of a combination that may be provided is between the sheath and the dissecting instrument. In some instances, the sheath itself may serve as the dissecting instrument and provide one or more channels for the delivery of other instruments in connection with the present invention. In yet another example, the vein closure device itself may incorporate a vision or imaging system to allow the practitioner to visually monitor the procedure.

The vein closure devices of the present invention may preferably be constructed according to the principles used in manufacturing devices for abdominal laparoscopy. A variety of companies produce instruments that could be modified to suit the needs of the present invention. The modifications to existing laparoscopic instruments may include, e.g., smaller diameters (e.g. 1-20 mm) and shorter lengths (e.g., 1-15 cm) to accommodate the different anatomy faced by a practitioner, in addition, the, clips and other closure devices may be modified. Potential examples of some suitable vein closure devices are described below.

United States Surgical Autosuture systems provide a number of devices that may be capable of adaptation for use in connection with the present invention. U.S. Pat. No. 5,833,696 (Whitfield et al.) describes some clip instruments that in may be used as a vein closure device in the present invention with some modifications. Commercially available examples may include, e.g., Accuclip Right-angle multiple applier with titanium clips; Endoclip 5 mm (No. 176620); Endoclip 10 mm pistol grip (No. 176615); Endoclip II 10 mm pistol grip (No. 176657); and Endoclip multiapplier (No. 50011a). U.S. Pat. No. 4,101,063 (Kapitanov) also discloses a device for ligating tubular organs using staples.

Other potentially suitable devices may include those marketed by Ethicon Endo-surgery (Johnson and Johnson) for endoligation, such as the LIGACLIP ERCA endoscopic rotating instruments (ER 200, ER 320, ER420) or ALLPORT appliers (AL 236, AL 326). Still other potentially suitable devices may include the INTERCEPTRE Modular Laparoscopic instruments made by Smith and Nephew. Other potentially suitable instruments could be based on designs such as those used in Olympus hand instruments and RFQ—Medizintechnik (which markets an endoscopic clip applying forceps for Ethicon clips (35-10100-100); and Horizon (No. 338110).

One exemplary procedure according to the principles of the present invention will now be described. The procedure may preferably be performed under local anesthesia administered to the skin and subcutaneous tissues of the inguinal fold above the saphenofemoral junction. Initial anesthesia would preferably be administered by needle injection, followed (if desired) by low volume local anesthetic infusion from the port within the dissecting insert.

The saphenofemoral junction and proximal saphenous vein would be identified with duplex ultrasound. A small incision would be made in the inguinal fold. The dissecting instrument could be used for direct dissection of soft tissues and fascia to access the proximal saphenous vein or the outer sheath with dissecting insert installed would be inserted through the subcutaneous tissue to the proximal saphenous vein, 2 centimeters distal to the saphenofemoral junction. Low volume local anesthesia with 2% lidocaine would be administered during duplex guided positioning of the outer tube/dissecting insert near the target point for clipping on the 2 centimeters distal to the saphenofemoral junction. The dissecting insert would be withdrawn and the vein closure device would be inserted through the outer sheath or directly into the tissue for the direct approach.

The vein closure device (e.g., clipping jaws would be opened and advanced to surround the target point and then used to close the proximal saphenous vein at that point. With the clipping device still attached to the proximal saphenous vein and under duplex ultrasound guidance, an appropriate sclerotherapy needle (such as a 10 centimeter 25 gauge needle or other needle design included as a part of the kit/system) would be used to perform retrograde sclerotherapy of the distal saphenous vein with 0.5-3% sodium tetradecyl sulfate or other sclerosant. The final sclerosant could be, e.g., STS foam to permit stabilization of the sclerosant at the proximal portion of the saphenous vein. Performing the sclerotherapy while still holding the proximal vein will preferably allow security for easier access to the saphenous lumen.

As is current standard practice, after ablation of the saphenofemoral junction and saphenous vein from groin to knee, standard sclerotherapy or ambulatory phlebectomy of tributary varicosities may then be performed during the same operation. Standard compression stockings would be placed and worn for 1-3 weeks. Immediate postoperative ambulation would be permitted. The only restrictions postoperatively would be no aerobic exercise or heavy lifting for one week.

Although described above with respect to treatment of the saphenofemoral junction and corresponding distal saphenous vein, the devices, kits and methods of the present invention may also be used as discussed herein to treat an incompetent saphenopopliteal junction and its corresponding lesser or short saphenous vein.

In yet another variation, the devices, kits and methods of the present invention may also be used to close (e.g., clip/ligate, etc.) large distal tributary varicose veins (or any other selected vein) and then perform retrograde sclerotherapy. Such a procedure may retain the sclerosant within the vein longer, which may result in more complete sclerosis and obliteration of the vein.

As used herein and in the appended claims, the singular forms "a," "and," and "the" include plural references unless explicitly limited to the singular form or the context clearly dictates otherwise.

All references and publications cited herein are expressly incorporated herein by reference in their entirety into this disclosure (to the extent that they are not inconsistent with this disclosure). Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of treating an incompetent venous junction, the method comprising:
    advancing a distal end of an elongated sheath to a position proximate a vein;
    advancing a vein closure device through the elongated sheath towards the distal end of the elongated sheath;
    grasping the vein at a location distal to the incompetent venous junction;
    advancing a needle out of an injection port of an injection channel of the elongated sheath, wherein the injection channel defines an injection direction that is not aligned with a longitudinal axis of the elongated sheath, whereby the needle extends out of the injection channel from the injection port along the injection direction; and
    injecting a sclerosing agent into the vein at an injection site that is distal of the location at which the vein is grasped, wherein the injecting is performed using the needle advanced out of the injection port.

2. A method according to claim 1, wherein the injection direction forms an injection angle with the longitudinal axis that is greater than five (5) degrees.

3. A method according to claim 1, further comprising closing the vein at a location distal of the incompetent venous junction and proximal of the injection site using the vein closure device.

4. A method according to claim 1, further comprising withdrawing the needle into the injection channel after the injecting.

5. A method according to claim 1, further comprising withdrawing the vein closure device and the elongated sheath.

6. A method according to claim 1, further comprising visually monitoring the positioning of the elongated sheath, the vein closure device, and the needle using ultrasonic energy.

7. A method according to claim 1, wherein advancing the needle out of the injection port comprises advancing the needle into the vein after grasping the vein at the location distal to the incompetent venous junction.

8. A method according to claim 1, wherein advancing the needle out of the injection port comprises advancing the needle into the vein from an exterior of the vein after grasping the vein at the location distal to the incompetent venous junction.

9. A method according to claim 1, wherein advancing the needle out of the injection port comprises advancing a tip of the needle into the vein from an exterior of the vein after grasping the vein at the location distal to the incompetent venous junction.

10. A method according to claim 1, further comprising closing the vein at a location distal of the incompetent venous junction and proximal of the injection site using the vein closure device.

11. A method according to claim 1, further comprising withdrawing the needle into the injection channel after the injecting, wherein the needle is located outside of the vein whenever the needle is in the injection channel.

12. A method according to claim 11, further comprising withdrawing the vein closure device and the elongated sheath after withdrawing the needle into the injection channel.

13. A method of treating an incompetent venous junction, the method comprising:
    advancing a distal end of an elongated sheath to a position proximate an exterior surface of a vein;
    advancing a vein closure device through the elongated sheath towards the distal end of the elongated sheath;
    grasping the exterior surface of the vein at a location distal to the incompetent venous junction;
    advancing a needle out of an injection port of an injection channel of the elongated sheath and into the vein after grasping the vein, wherein advancing the needle moves a tip of the needle into the vein through an injection site on the exterior surface of the vein, wherein the injection site is distal of the location at which the vein is grasped, and wherein the injection channel defines an injection direction that is not aligned with a longitudinal axis of the elongated sheath, whereby the needle extends out of the injection channel from the injection port along the injection direction; and
    injecting a sclerosing agent into the vein through the needle after advancing the tip of the needle into the vein.

14. A method according to claim 13, wherein the injection direction forms an injection angle with the longitudinal axis that is greater than five (5) degrees.

15. A method according to claim 13, further comprising visually monitoring the positioning of the elongated sheath, the vein closure device, and the needle using ultrasonic energy.

* * * * *